(12) United States Patent
Li (10) Patent No.: US 12,329,938 B2
(45) Date of Patent: Jun. 17, 2025

(54) ELECTROCHEMICAL PUMP UNIT OF MESH COMBINED ELECTRODE

(71) Applicant: MicroMED Co., Ltd., Taipei (TW)

(72) Inventor: Po-Ying Li, Taipei (TW)

(73) Assignee: MICROMED CO., LTD., Taipei (TW)

(*) Notice: Subject to any disclaimer, the term of this patent is extended or adjusted under 35 U.S.C. 154(b) by 830 days.

(21) Appl. No.: 17/518,044

(22) Filed: Nov. 3, 2021

(65) Prior Publication Data

US 2022/0152290 A1    May 19, 2022

Related U.S. Application Data

(60) Provisional application No. 63/115,223, filed on Nov. 18, 2020.

(51) Int. Cl.
| | |
|---|---|
| *A61M 5/20* | (2006.01) |
| *A61M 5/145* | (2006.01) |
| *A61M 5/142* | (2006.01) |
| *A61M 5/315* | (2006.01) |

(52) U.S. Cl.
CPC ........ *A61M 5/2046* (2013.01); *A61M 5/1452* (2013.01); *A61M 2005/14204* (2013.01); *A61M 5/31513* (2013.01)

(58) Field of Classification Search
CPC .............. A61M 5/2046; A61M 5/1452; A61M 2005/14204; A61M 5/145; H01G 11/00
See application file for complete search history.

(56) References Cited

U.S. PATENT DOCUMENTS

| | | | | |
|---|---|---|---|---|
| 3,379,634 | A  * | 4/1968 | Rutkowski | C25B 9/73 204/266 |
| 6,450,991 | B1 * | 9/2002 | Bunt | A61K 9/0009 604/141 |
| 8,353,426 | B2 * | 1/2013 | Wold | A61M 11/007 222/1 |
| 2010/0222770 | A1 * | 9/2010 | Gordon | A61M 5/14276 604/151 |
| 2012/0040254 | A1 * | 2/2012 | Amendola | H01M 4/8615 977/734 |
| 2014/0239310 | A1 * | 8/2014 | Rho | H01L 33/0075 438/47 |
| 2015/0144132 | A1 * | 5/2015 | Satoh | A61M 16/0057 128/202.26 |
| 2016/0089490 | A1 * | 3/2016 | Foulds | A61M 5/142 604/84 |

* cited by examiner

*Primary Examiner* — Nilay J Shah (74) *Attorney, Agent, or Firm* — Muncy, Geissler, Olds & Lowe, P.C.

(57) ABSTRACT

The electrochemical pump unit of mesh combined electrode of the present invention is connected to a drug injection container for operation, when it is connected to the power supply, the cathode (or anode) enters into electrochemical reaction with the electrolyte of the superabsorbent material layer through the mesh electrode to release a first gas, the first gas flows through the screen meshes of mesh electrode immediately without obstruction loss; the anode (or cathode) enters into electrochemical reaction with the electrolyte on the opposite side of superabsorbent material layer through the plane electrode to release a second gas, the second gas flows through the inter fibrous small space/channels of superabsorbent material layer and the screen meshes of mesh electrode; as the first gas and the second gas increase, the piston is pushed, and the medicament is pushed.

7 Claims, 10 Drawing Sheets

ELECTROCHEMICAL PUMP UNIT OF MESH COMBINED ELECTRODE

CROSS-REFERENCE TO RELATED APPLICATIONS

This Non-provisional application claims priority under 35 U.S.C. § 119(a) on Patent Application No. [63/115,223] filed in American United Sates Nov. 18, 2020, the entire contents of which are hereby incorporated by reference.

FIELD OF THE INVENTION

The present invention relates to the domain of electrochemical pump for relieving gas pressure, and more particularly to an electrochemical pump unit of mesh combined electrode using electrochemical pump of mesh electrode.

BACKGROUND OF INVENTION

The treatment of many chronic diseases requires accurately controlled dosage of drugs, the drug or therapeutic agent is applied hypodermically at continuous or specific time intervals. Additionally, some treatments require a shot volume larger than 1 ml, exceeding the limit of the injection volume of the existing hypodermic injection device, and the injection speed is too fast (several seconds) or too slow (several hours); for example, the shot volume of intravenous injection of traditional protein drugs is usually larger than 30 mL, even 250 mL, the injection time is 30 minutes to several hours.

Many wearable drug pump units are driven by stepping motors (or similar components for rotating gears), but their motion is discrete (one step each time), not continuous. Therefore, the basic delivery flow provided by the stepping motor is discrete (one droplet each time). For example, the basic speed within 5 to 5000 nl/min (typical dosage regimen of insulin) has discrete delivery of 5 mL each time, the speed is one delivery per hour to one thousand deliveries per hour, the injection of 1 mL usually exceeds 3-6 hours, this injection speed is too slow to meet the patients' requirement (5-10 minutes).

The interdigital microelectrodes are extensively used in electrochemical sensors and actuators, due to the static friction of bubbles (surface tension between bubbles and electrode), these 2D electrodes are actually difficult to discharge the gas generated on the microelectrode surface. The static friction of bubbles increases the total voltage (resistance) between anode and cathode of plane electrode, and increases the power consumption of control circuit. The addition of hydrophilic material (e.g. high water absorption material) contributes to effectively removing the bubbles generated on the electrode surface, so as to reduce the electrode voltage and power consumption. This adsorbing material can effectively remove gas in medium and low gas production conditions (<100 μL/min). However, when higher gas removal rate (>100 μL/min) is required, a new electrode chamber design with higher gas removal rate is required.

The existing electrochemical pump usually uses two plate electrodes to generate gas, as the plate electrodes are located on both sides of a large area, the generated gas is forced to flee from the relatively narrow interlayer periphery, the released gas is turbulent, leading to unbalanced pressure between the two plate electrodes, failing to provide effective gas of linear and specific curves, so that the medicament supply cannot meet the patient's requirement. Therefore, it is very important to develop an electrochemical pump which can provide directional and quantitative gas production rate to supply drugs, and can achieve supply gas pressure of linear and specific curves.

SUMMARY OF THE INVENTION

In view of this, the present invention provides an electrochemical pump unit of mesh combined electrode in order to solve the prior technical problems, which can achieve the supply gas pressure of linear and specific curves to supply drugs.

Figure 1:
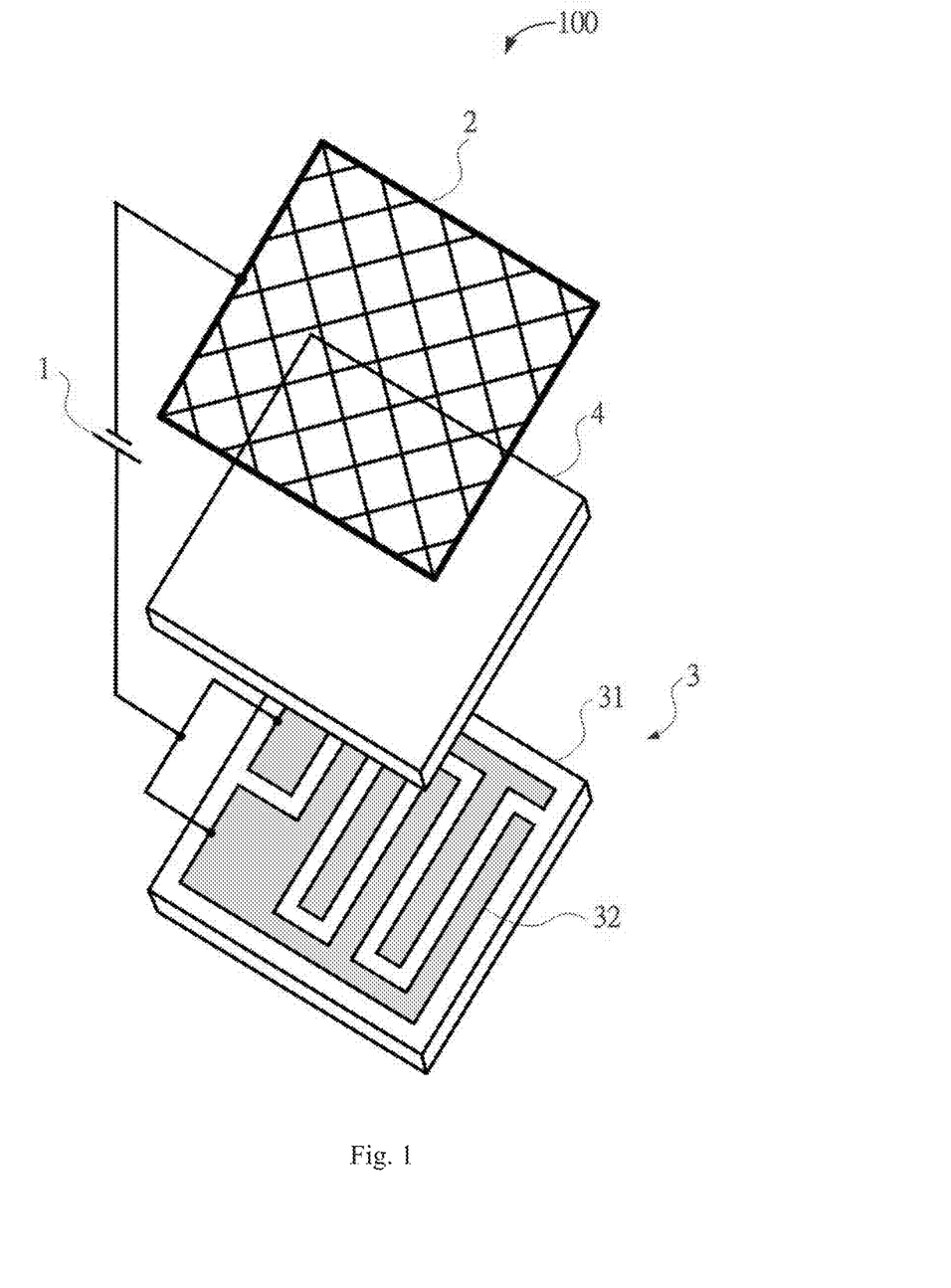
FIG. 1 Schematic diagram of electrochemical pump of mesh combined electrode.

As shown in [FIG. 1], an electrochemical pump of mesh combined electrode of the present invention includes a power supply, a mesh electrode, a second electrode and a superabsorbent material layer; the power supply provides working voltage for this device, it is connected to the mesh electrode and the second electrode; the superabsorbent material layer is sandwiched in between the mesh electrode and the second electrode, storing an electrolyte.

The electrolyte releases a gas after electrochemical reaction.

Figure 3:
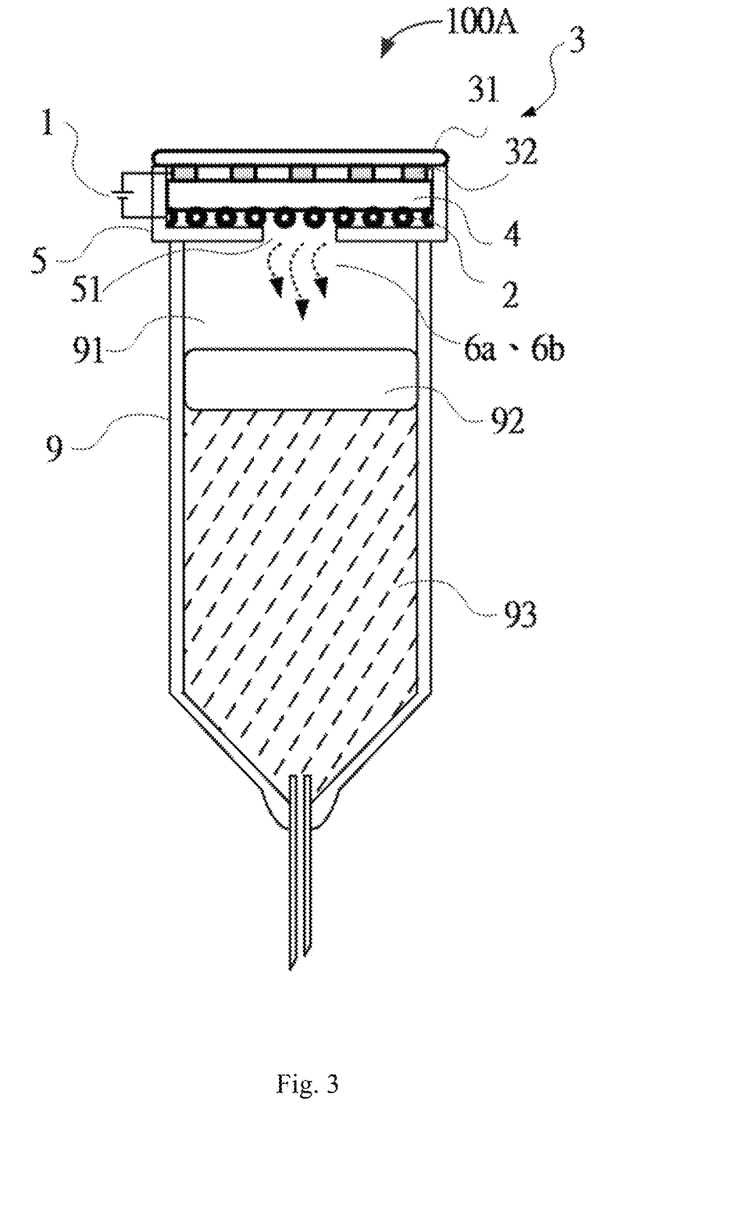
FIG. 3 Schematic diagram of electrochemical pump connected to drug injection container.

The electrochemical pump of mesh combined electrode of the present invention can be provided with an outer casing to form an electrochemical pump unit of mesh combined electrode; the outer casing wraps the mesh electrode, the second electrode and the superabsorbent material layer, the outer casing has a gas outlet adjacent to the mesh electrode, as shown in [FIG. 3].

Figure 2:
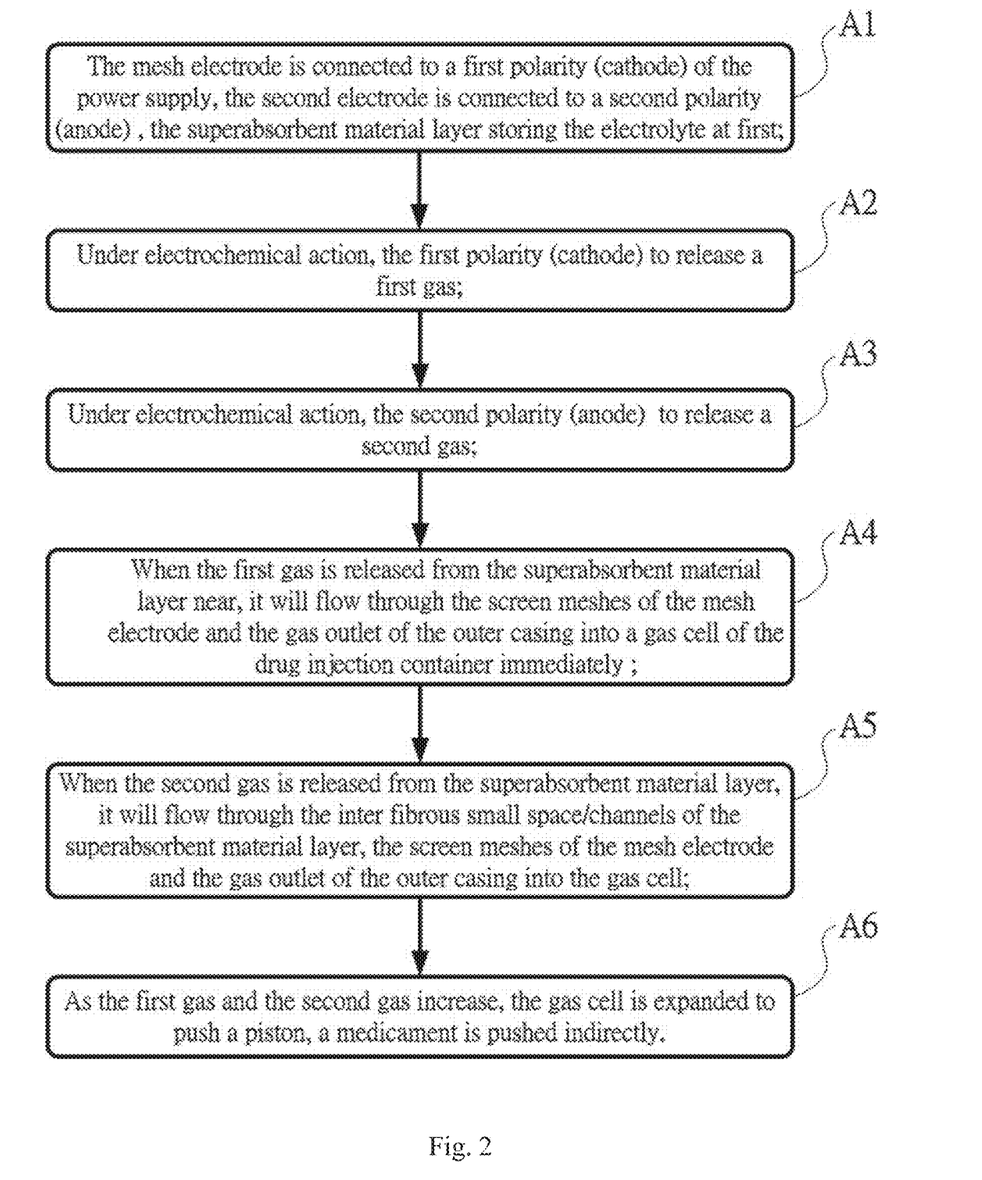
FIG. 2 Flow diagram of electrochemical pump unit of mesh combined electrode.

The electrochemical pump unit of mesh combined electrode of the present invention is used with a drug injection container, the operation process is shown in [FIG. 2] and [FIG. 3]:

A1. The mesh electrode is connected to a first polarity (e.g. cathode, negative pole) of the power supply, the second electrode is connected to a second polarity (e.g. anode, positive pole) of the power supply, the second electrode in this embodiment is a plane electrode, the superabsorbent material layer is sandwiched in between the mesh electrode and the second electrode, the superabsorbent material layer storing the electrolyte (DI water with salts, e.g. NaCl, CaCl2), KCl) at first;

A2. Under electrochemical action, the first polarity (e.g. cathode) enters into electrochemical reaction with the electrolyte (e.g.) to release a gas which is a first gas (e.g. H2) through the mesh electrode and one side of the superabsorbent material layer;

A3. The second polarity (e.g. anode) enters into electrochemical reaction with the electrolyte to release the gas which is a second gas (e.g. O2) through the second electrode and the opposite side of the superabsorbent material layer;

A4. When the first gas (e.g. H2) is released from the end of the superabsorbent material layer near the mesh electrode, it will flow through the screen meshes of the mesh electrode and the gas outlet of the outer casing into a gas cell of the drug injection container immediately without obstruction loss, there is one layer of obstruction loss less than the existing technology;

A5. When the second gas (e.g. O2) is released from the end of the superabsorbent material layer near the second electrode, it will flow through the inter fibrous small space/channels of the superabsorbent material layer, the screen meshes of the mesh electrode and the gas outlet of the outer casing into the gas cell; there will be a little loss when the gas flows through the fibers of the superabsorbent material layer, the obstruction loss is lower than the existing technology; and A6. As the first gas (e.g. H2) and the second gas (e.g. O2) increase, the gas cell is expanded to push a piston, a medicament is pushed indirectly.

Preferably, an embodiment of electrochemical formula is:

Cathode: $2H_2O_{(l)} \rightarrow O_{2(g)} + 4H_{(aq)}^+ + 4e^-$

Anode: $4H_{(aq)}^+ + 4e^- \rightarrow 2H_{2(g)}$

Net: $2H_2O_{(l)} \rightarrow O_{2(g)} + 2H_{2(g)}$.

Preferably, the superabsorbent material layer absorbs the electrochemical gas generating liquid, the area of electrochemical reaction and the gas flow rate generated by electrochemical reaction can be controlled.

Figure 9:
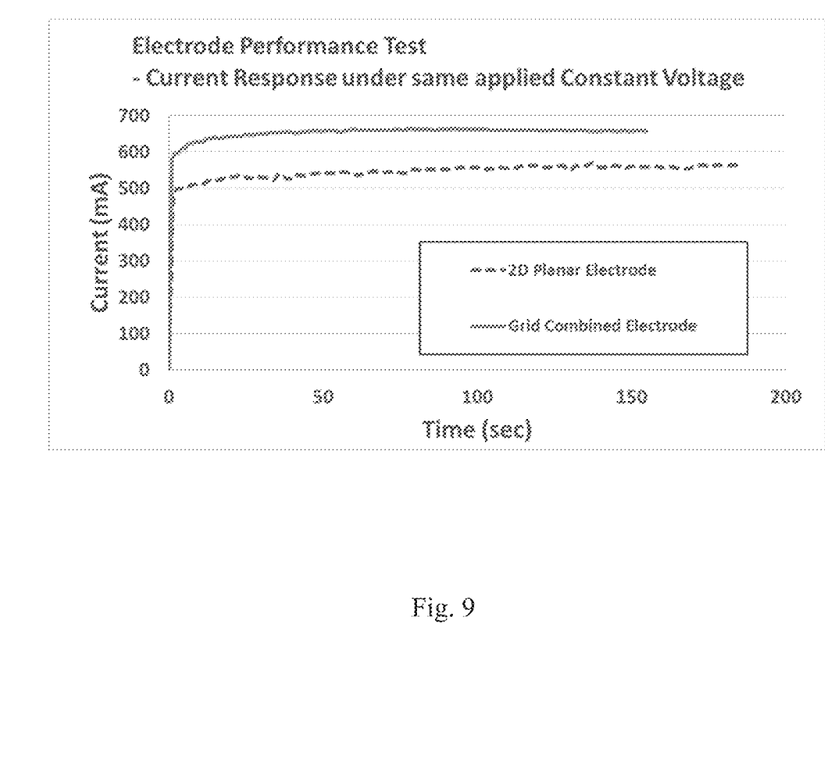
FIG. 9 Electrode performance test—current diagram.
Figure 10:
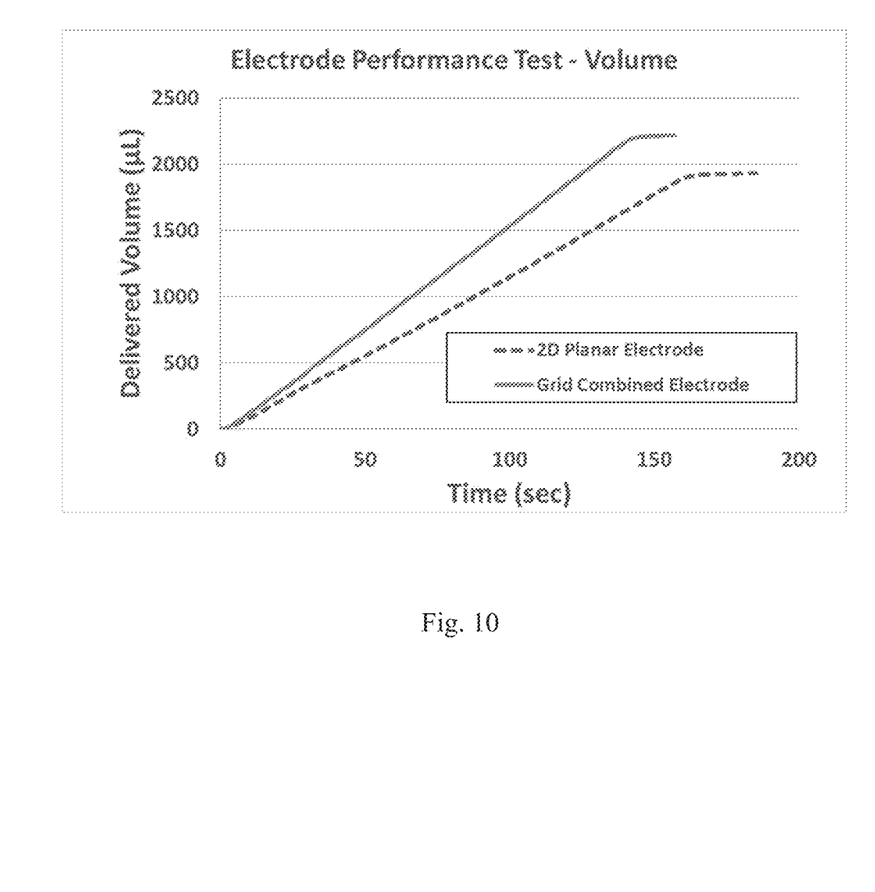
FIG. 10 Electrode performance test—volume diagram.

It is noteworthy that the gas discharge rate of the electrochemical pump of mesh combined electrode of the present invention is several times of the bi electrode structure of the present technology, so as to reduce the voltage and power consumption of electrochemical system; as shown in [FIG. 9], in the electrode performance test, this system has higher current response than the present technology in the same additional constant pressure condition; as shown in [FIG. 10], in the electrode performance test, this system generates larger gas volume by electrochemistry than the present technology in the same condition.

DETAILED DESCRIPTION OF THE INVENTION

Figure 5:
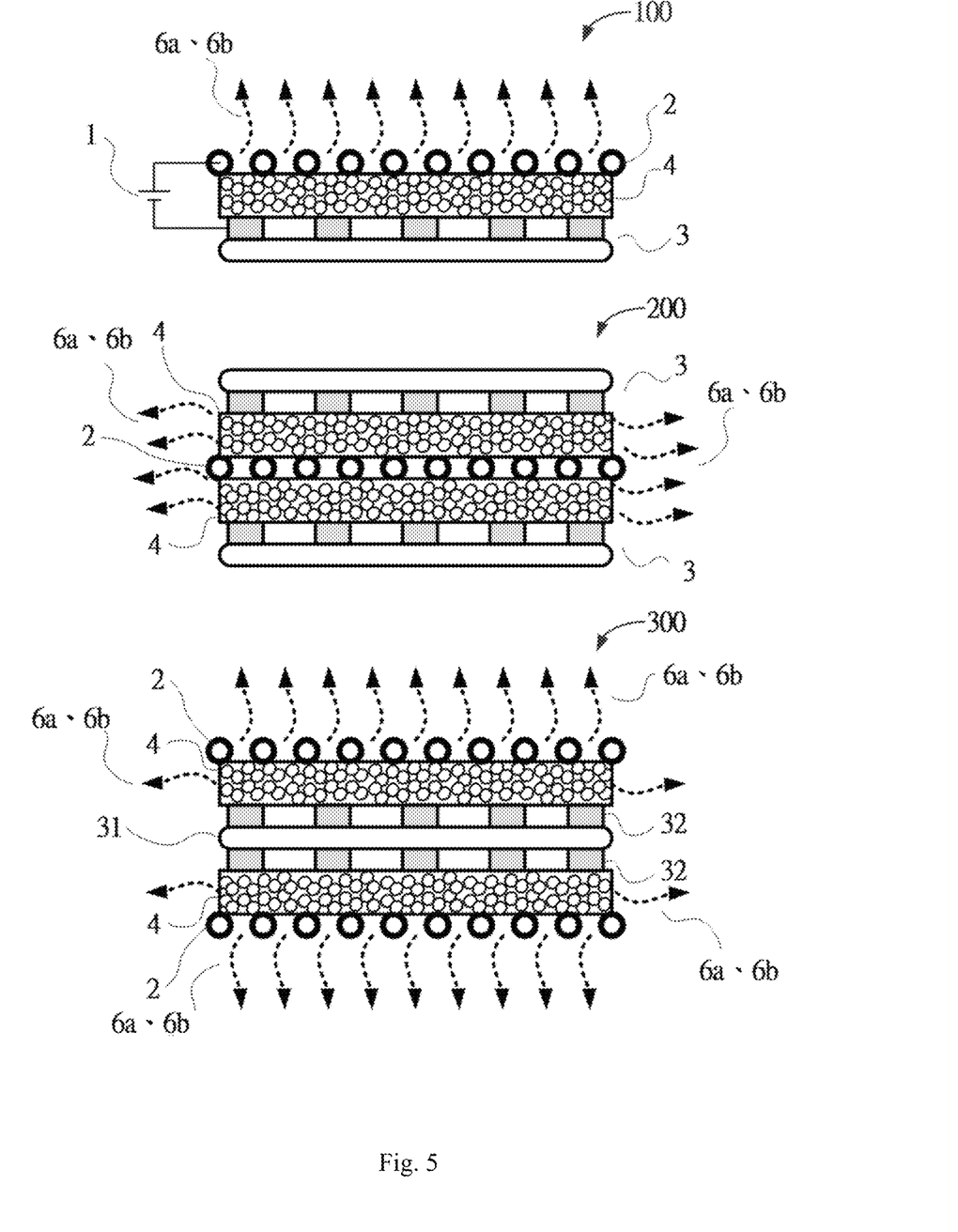
FIG. 5 Schematic diagram of electrochemical pumps of different combinations.

An embodiment of the present invention, an electrochemical pump of mesh combined electrode 100 is connected to a power supply 1, the electrochemical pump 100 is shown in [FIG. 1] and [FIG. 5], including:

A mesh electrode 2, connected to a first polarity of the power supply 1, the electrochemical reaction generates a gas 6a which is a first gas (e.g. H2), the first gas can flow through the screen meshes of the mesh electrode 2 without obstruction loss;

A second electrode 3, connected to a second polarity of the power supply 1, the second electrode 3 in this embodiment is a plane electrode 30 composed of a substrate layer 31 and an electrode layer 32, the electrochemical reaction generates the gas 6b which is a second gas (e.g. O2), the second gas flows through the inter fibrous small space/channels of the superabsorbent material layer 4 and the screen meshes of the mesh electrode 2;

A superabsorbent material layer 4, located between the mesh electrode 2 and the second electrode 3, the superabsorbent material layer 4 stores an electrolyte (DI water with salts, e.g. NaCl, $CaCl_2$, KCl . . . ); and The superabsorbent material layer 4 is sandwiched in between the mesh electrode 2 and the second electrode 3, the first gas and the second gas are discharged from the mesh electrode 2.

The electrochemical pump of mesh combined electrode 100 of the present invention can provide a gas discharge rate several times higher than the bi electrode structure of the present technology, so as to reduce the voltage and power consumption of electrochemical system.

In the said embodiment, if the first polarity is positive pole (anode), the second polarity is negative pole (cathode); if the first polarity is negative pole (cathode), the second polarity is positive pole (anode).

Preferably, the electrolyte materials include hydroxide electrolyte, aqueous solution of water and salt, acid or alkali, and non aqueous ion solution, ethanol.

Preferably, the mesh electrode 2 comprises a plurality of screen meshes formed by multiple cross and interconnected mesh lines.

Preferably, the power supply 1 includes mercury cell, lithium battery, carbon-zinc battery and power supply which can provide a voltage.

Preferably, the mesh electrode materials include Pt, Ti, Au, IrO2, Ag, C and Pd and any electrode materials.

An embodiment of the present invention, the second electrode 3 includes the substrate layer 31 and the electrode layer 32, the substrate layer 31 can be a hard substrate, a flexible substrate or a porous substrate.

Preferably, the substrate layer 31 is the hard substrate material, including hard glass substrate, sapphire substrate, transparent ceramic substrate or other appropriate substrates; the substrate layer is the flexible substrate material, including thin glass substrate or polymer flexible substrate.

Preferably, the materials of the electrode layer 32 include Pt, Ti, Au, IrO2, Ag, C and Pd and any electrode materials.

Preferably, the material of the superabsorbent material layer 4 can be any absorbent material, e.g. solid phase of gel, cotton, superabsorbent polymer, sponge material or an arbitrary combination (e.g. gel absorbed in sponge); its function is to maintain the uniform distribution of electrolyte in the entire superabsorbent material layer 4, and to maintain contact with the electrode.

An embodiment of the present invention, the second electrode 3 can be the mesh electrode 2 or the second electrode 3 composed of screen mesh shape and size different from the mesh electrode 2.

Preferably, the gas 6a, 6b generated by the first polarity and the second polarity under electrochemical action includes the combination of hydrogen, oxygen and/or CO2; for example, the electrolysis of water generates oxygen and hydrogen, the electrolysis of ethanol generates CO2 and hydrogen; the power consumption of electrolytic pump can be reduced by using ethanol, the battery lifetime is extended.

Figure 4:
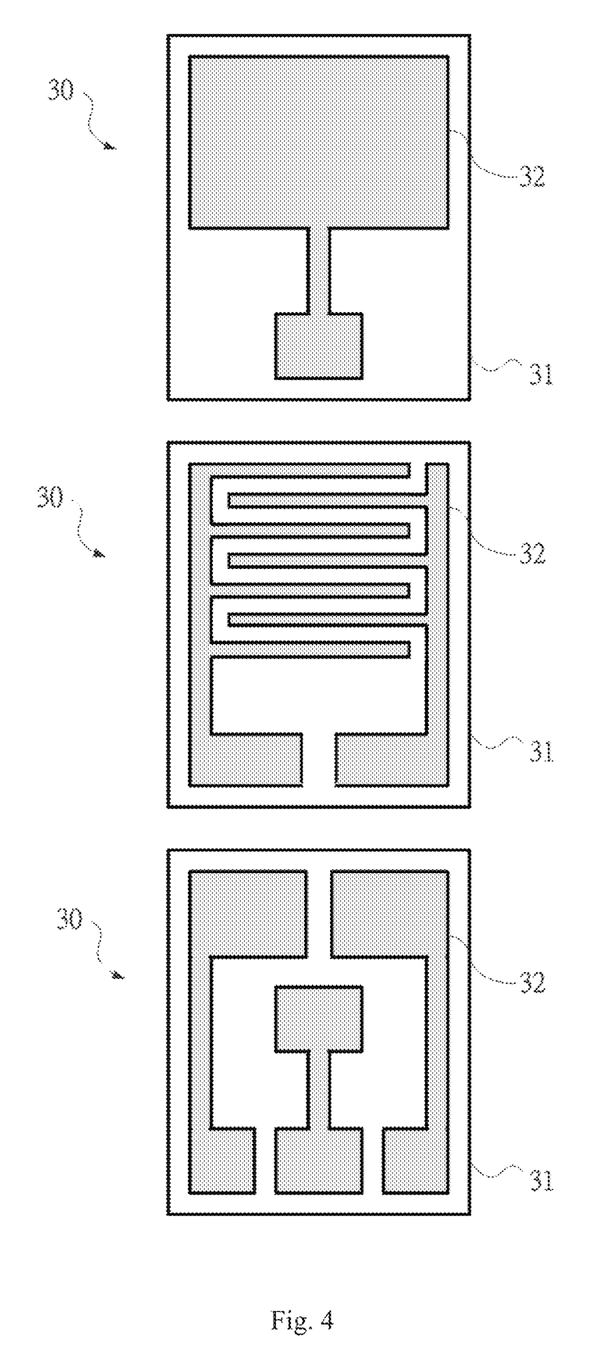
FIG. 4 Schematic diagram of three embodiments of plane electrode.

An embodiment of the present invention, as shown in [FIG. 4], the second electrode 3 includes the plane electrode 30, e.g. rectangular electrode (one electrode), interdigital electrode (two electrodes), cathode-anode-reference electrode (three electrodes), but the present invention is not limited to them.

Preferably, the screen meshes formed by multiple mesh lines of the mesh electrode 2 include interdigital, square, rectangular, quadrangular, honeycomb and polygonal meshes.

An embodiment of the present invention, an electrochemical pump of mesh combined electrode 200 is connected to a power supply 1, as shown in the middle part of [FIG. 5]:

A mesh electrode 2, connected to a first polarity of the power supply 1, the electrochemical reaction generates a gas 6a which is a first gas;

A second electrode 3, the second electrode 3 in this embodiment has two layers, it is a plane electrode 30 composed of a substrate layer 31 and an electrode layer 32, two layers of the plane electrode 30 are connected to a second polarity of the power supply 1 respectively, the electrochemical reaction generates the gas 6b which is a second gas;

A superabsorbent material layer 4, the superabsorbent material layer 4 has two layers, storing an electrolyte; and upper and lower outer layers are the substrate layer 31 of the second electrode 3, connected to the electrode layer 32, the superabsorbent material layer 4 and the mesh electrode 2 inwards respectively, the mesh electrode 2 has one layer, the rest has two layers vertically corresponding to each other; the first gas and the second gas are discharged from the side edge through the inter fibrous small space/channels of the superabsorbent material layer 4.

In the said embodiment, the substrate layer 31 of two layers of the plane electrode 30 is a porous substrate, the first gas and the second gas can be discharged through the holes in the substrate layer 31.

An embodiment of the present invention, an electrochemical pump of mesh combined electrode 300 is connected to a power supply 1, as shown in the lower part of [FIG. 5]:

A mesh electrode 2, there are two layers of the mesh electrode 2 in this embodiment, connected to a first polarity of the power supply 1 respectively, the electrochemical reaction generates a gas 6a which is a first gas, the first gas can flow through the screen meshes of the upper and lower mesh electrodes 2 without obstruction loss;

A second electrode 3, the second electrode 3 in this embodiment is a double sided plane electrode 30 composed of a substrate layer 31 and upper and lower electrode layers 32, connected to a second polarity of the power supply 1, the electrochemical reaction generates the gas 6b which is a second gas, the second gas flows through the inter fibrous small space/channels of the upper and lower superabsorbent material layers 4 and through the screen meshes of the upper and lower mesh electrodes 2;

A superabsorbent material layer 4, the superabsorbent material layer 4 has two layers, storing an electrolyte; and upper and lower outer layers are connected to the superabsorbent material layer 4, the electrode layer 32 and the substrate layer 31 inwards respectively for the mesh electrode 2, there is one of the substrate layer 31, the rest has two layers vertically corresponding to each other; the first gas and the second gas are discharged from the upper and lower mesh electrodes 2 and periphery.

In the said embodiment, the operation process is described below:

B1. The mesh electrode 2 is connected to a first polarity of a power supply 1, two layers of the electrode layer 32 are connected to a second polarity anode of the power supply 1;

B2. The cathode enters into electrochemical reaction with the electrolyte on one side of the upper superabsorbent material layer 4 through the upper mesh electrode 2 to release a first gas; when the first gas is released from the end of the upper superabsorbent material layer 4 near the upper mesh electrode 2, it will be released upwards through the screen meshes of the upper mesh electrode 2 immediately without obstruction loss;

B3. The cathode enters into electrochemical reaction with the electrolyte on one side of the lower superabsorbent material layer 4 through the lower mesh electrode 2 to release a first gas; when the first gas is released from the end of the lower superabsorbent material layer 4 near the lower mesh electrode 2, it will be released downwards through the screen meshes of the lower mesh electrode 2 immediately without obstruction loss;

B4. The anode enters into electrochemical reaction with the electrolyte on one side of the upper superabsorbent material layer 4 through the upper electrode layer 32 to release a second gas; when the second gas is released from the end of the upper superabsorbent material layer 4 near the upper electrode layer 32, it is released from the side edge or/and through the inter fibrous small space/channels of the upper superabsorbent material layer 4 and released upwards through the screen meshes of the upper mesh electrode 2;

B5. The anode enters into electrochemical reaction with the electrolyte on one side of the lower superabsorbent material layer 4 through the lower electrode layer 32 to release the second gas; when the second gas is released from the end of the lower superabsorbent material layer 4 near the lower electrode layer 32, it is released from the side edge or/and through the inter fibrous small space/channels of the lower superabsorbent material layer 4 and released downwards through the screen meshes of the lower mesh electrode 2; and B6. The electrochemical pump of mesh combined electrode 300 releases the gas 6a, 6b from periphery.

Figure 6:
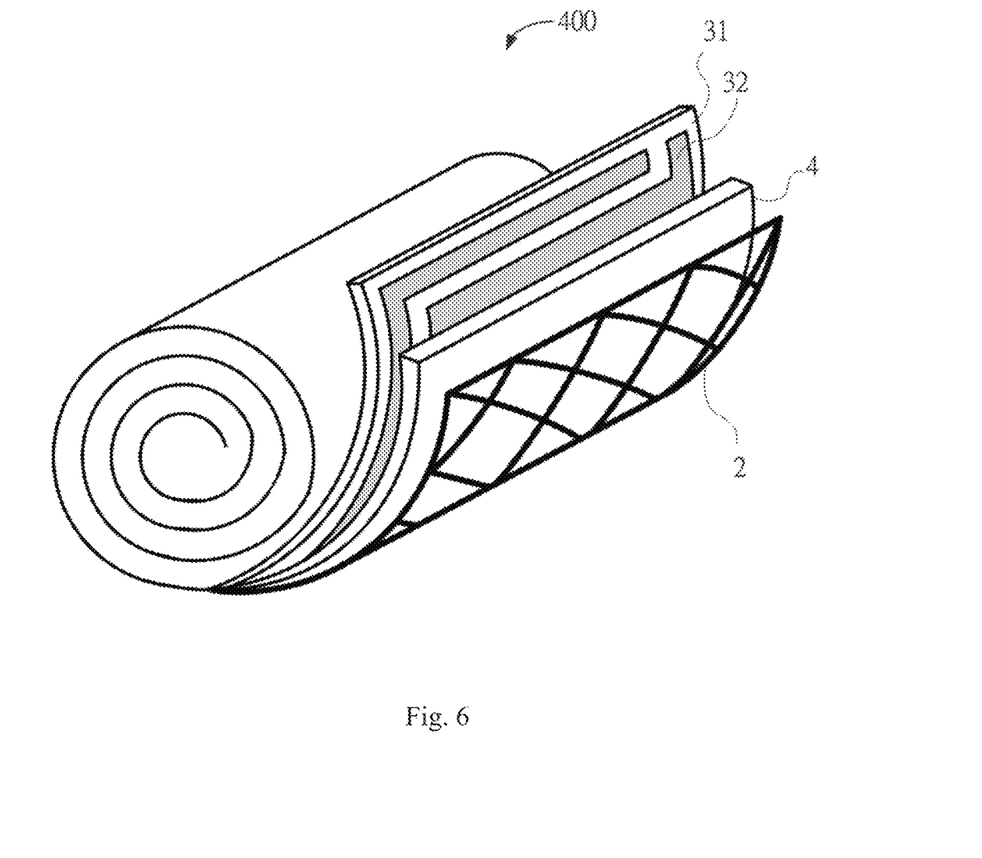
FIG. 6 Schematic diagram of Roll-up electrochemical pump of mesh combined electrode.

An embodiment of the present invention, an electrochemical pump of mesh combined electrode is connected to a power supply 1, as shown in [FIG. 6]:

A mesh electrode 2, connected to a first polarity of the power supply 1, the electrochemical reaction generates a gas 6a which is a first gas;

A second electrode 3, connected to a second polarity of the power supply 1, the second electrode 3 in this embodiment is a plane electrode 30 composed of a substrate layer 31 of reelable porous substrate material and an Roll-up electrode layer 32, the gas 6b generated by electrochemical reaction is a second gas;

A superabsorbent material layer 4, located between the mesh electrode 2 and the second electrode 3, the superabsorbent material layer 4 stores an electrolyte; and The outer layer is the mesh electrode 2, the middle layer is the superabsorbent material layer 4 and the inner layer is the second electrode 3, the three layers are rolled up to form a winding cylindrical pump 400, the first gas and the second gas in the inner layer flow through the inter fibrous small space/channels of the superabsorbent material layer 4 and the holes in the substrate layer 31, and then they are discharged from the outer mesh electrode 2.

In the said embodiment, the second electrode 3 of the winding cylindrical pump 400 can be composed of screen mesh shape and size different from or identical to the mesh electrode 2; this structure can reduce the obstruction loss when the first gas and the second gas are discharged from the inner layer.

Figure 7:
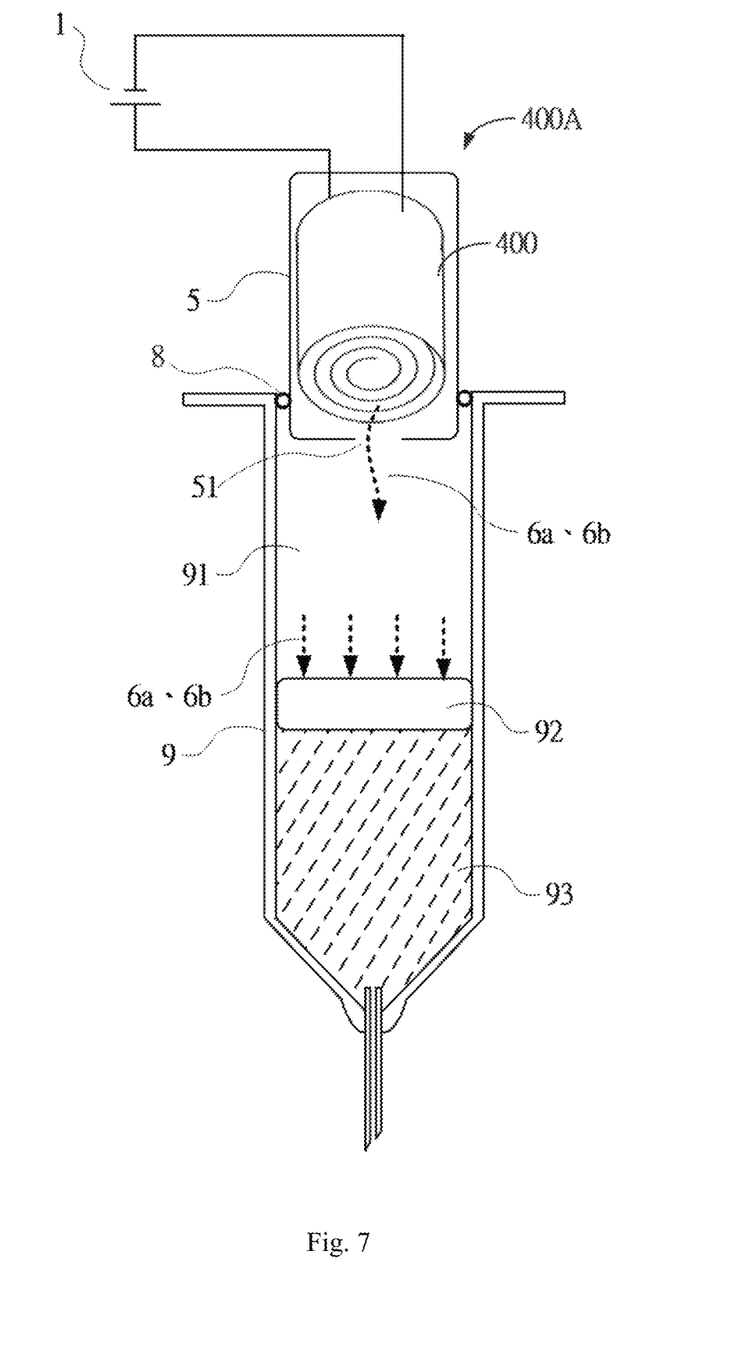
FIG. 7 Schematic diagram of winding electrochemical pump connected to drug injection container.

In the said embodiment, as shown in [FIG. 7], an electrochemical pump unit of mesh combined electrode 400A includes the winding cylindrical pump 400 and an outer casing 5; the electrochemical pump of mesh combined electrode 400A is used with a drug injection container 9, the gas 6a, 6b generated by electrochemical action flows through a gas outlet 51 of the outer casing 5 into a gas cell 91 of the drug injection container 9, the gas cell 91 expands as the gas 6a, 6b increases and pushes a piston 92, indirectly pushing a medicament 93.

As shown in [FIG. 7], the electrochemical pump unit of mesh combined electrode 400A is connected to the drug injection container 9 by an airtight spacer 8, the airtightness of the gas cell 91 is enhanced.

Figure 8:
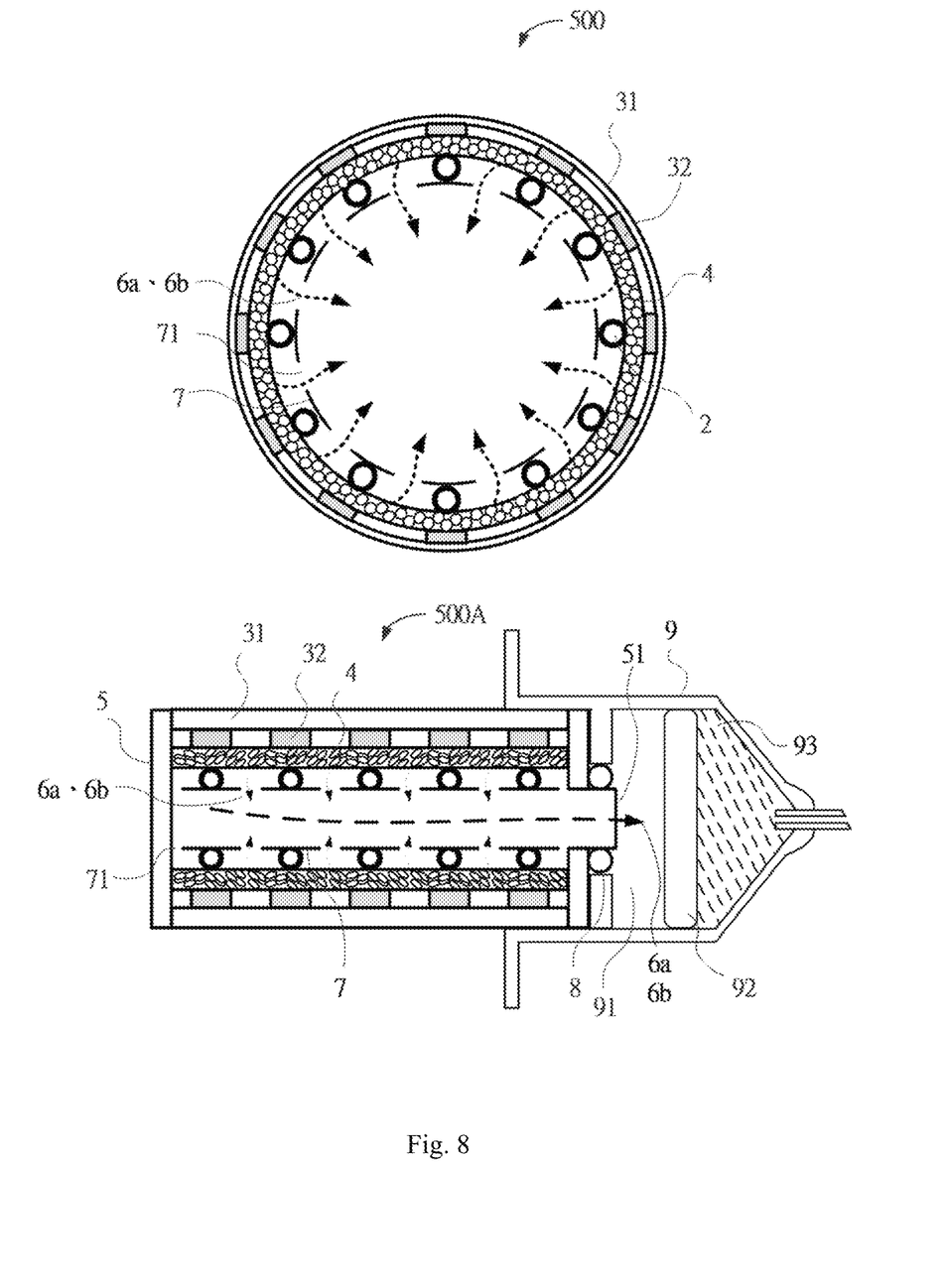
FIG. 8 Schematic diagram of circular electrochemical pump unit of mesh combined electrode.

An embodiment of the present invention, an electrochemical pump of mesh combined electrode is connected to a power supply 1, as shown in [FIG. 8]:

A mesh electrode 2, connected to a first polarity of the power supply 1, the electrochemical reaction generates a gas 6a which is a first gas;

A second electrode 3, connected to a second polarity of the power supply 1, the second electrode 3 in this embodiment is a plane electrode 30 composed of a substrate layer 31 of reelable substrate material and an Roll-up electrode layer 32, the gas 6b generated by electrochemical reaction is a second gas;

A superabsorbent material layer 4, located between the mesh electrode 2 and the second electrode 3, the superabsorbent material layer 4 stores an electrolyte; and The outer layer is the second electrode 3, the middle layer is the superabsorbent material layer 4 and the inner layer is the mesh electrode 2, the three layers are rolled up to form a hollow cylindrical pump 500, the first gas can flow through the screen meshes of the mesh electrode 2 to the center without obstruction loss, and the second gas flows through the inter fibrous small space/channels of the superabsorbent material layer 4 and the screen meshes of the mesh electrode 2 to the center.

In the said embodiment, as shown in [FIG. 7], an electrochemical pump unit of mesh combined electrode 500A includes the hollow cylindrical pump 500 and an outer casing 5; the electrochemical pump of mesh combined electrode 500A is used with a drug injection container 9, the gas 6a, 6b generated by electrochemical action flows into a gas cell 91 of the drug injection container 9 through a gas outlet 51 of the outer casing 5 from the center of the hollow cylindrical pump 500, the gas cell 91 expands as the gas 6a, 6b increases and pushes a piston 92, indirectly pushing a medicament 93.

In the said embodiment, a porous gas pipe 7 is installed in the middle of the hollow cylindrical pump 500, the gas 6a, 6b is led to the gas outlet 51 through a plurality of gas holes 71 in the wall of the porous gas pipe 7.

In the said embodiment, the porous gas pipe 7 can protrude from the outer casing 5, it can be inserted in the drug injection container 9 and sealed with an airtight spacer 8.

Preferably, the electrochemical pump of mesh combined electrode 500A can be designed as separate type, it is inserted in the drug injection container 9 before use.

The invention claimed is:

1. An electrochemical pump unit of mesh combined electrode connected to a power supply includes:
    a mesh electrode, connected to a first polarity of the power supply, wherein the mesh electrode is configured so that when a first electrochemical reaction generates a first gas, said first gas can flow through screen meshes of said mesh electrode;
    a second electrode, connected to a second polarity of the power supply, wherein the second electrode includes a plane electrode composed of a substrate layer and an electrode layer;
    a superabsorbent material layer, located between said mesh electrode and said second electrode, wherein said superabsorbent material layer stores an electrolyte and wherein the second electrode is configured so that when a second electrochemical reaction generates a second gas, said second gas flows through inter fibrous small space/channels of said superabsorbent material layer and said screen meshes of the mesh electrode; and
    an outer casing, wrapping said mesh electrode, said second electrode and said superabsorbent material layer, said outer casing includes a gas outlet, the first gas and the second gas are discharged from said gas outlet.

2. The electrochemical pump unit of mesh combined electrode defined in claim 1, wherein said substrate layer includes a flexible substrate.

3. The electrochemical pump unit of mesh combined electrode defined in claim 2, wherein said substrate layer of said second electrode is a porous substrate.

4. The electrochemical pump unit of mesh combined electrode defined in claim 1, further comprising an additional superabsorbent material layer and an additional second electrode, wherein the superabsorbent material layer and the additional superabsorbent material layer are located adjacent to the mesh electrode and on opposite sides of the mesh electrode, and wherein a side of the superabsorbent material layer is adjacent to a side of the second electrode and a side of the additional superabsorbent material layer is adjacent to a side of the additional second electrode.

5. The electrochemical pump unit of mesh combined electrode defined in claim 1, further comprising an additional superabsorbent material layer and an additional mesh electrode, wherein the superabsorbent material layer and the additional superabsorbent material layer are located adjacent to and on opposite sides of the second electrode, and wherein a side of the superabsorbent material laver is adjacent to a side of the mesh electrode and a side of the additional superabsorbent material layer is adjacent to a side of the additional mesh electrode, and wherein the substrate layer is connected to the electrode layer.

6. The electrochemical pump unit of mesh combined electrode defined in claim 1, wherein said outer casing is connected to a drug injection container for operation, said first gas and said second gas are discharged from said gas outlet to push the piston of the drug injection container, a medicament is pushed indirectly.

7. The electrochemical pump unit of mesh combined electrode defined in claim 1, wherein said second electrode includes a structure selected from the group consisting of a rectangular electrode, an interdigital electrode, and a cathode-anode-reference electrode.

* * * * *